Figure 1:
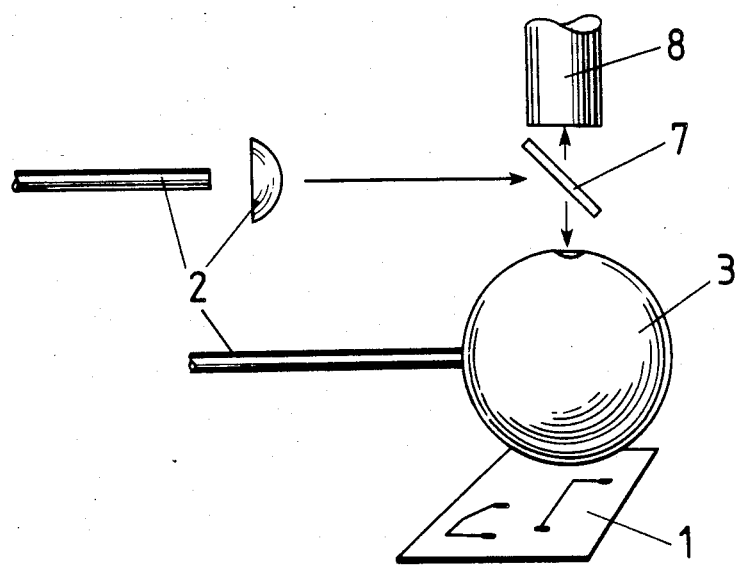

United States Patent [19]

Piironen

[11] Patent Number: 4,651,262
[45] Date of Patent: Mar. 17, 1987

[54] LIGHTING DEVICE

[75] Inventor: Timo H. Piironen, Oulu, Finland

[73] Assignee: Valtion teknillinen tutkimuskeskus, Espoo, Finland

[21] Appl. No.: 813,942

[22] Filed: Dec. 27, 1985

[30] Foreign Application Priority Data

Dec. 31, 1984 [FI] Finland .................................. 845176

[51] Int. Cl.$^4$ ............................................. F21V 7/00
[52] U.S. Cl. ..................... 362/350; 362/16; 362/809; 362/458; 362/356; 362/297; 362/347; 354/126
[58] Field of Search ................. 362/350, 458, 809, 16, 362/317, 391, 296, 297, 298, 301; 356/213; 354/126, 132, 150

[56] References Cited

U.S. PATENT DOCUMENTS

| | | | |
|---|---|---|---|
| 1,711,478 | 4/1929 | Halvorson, Jr. ..................... | 362/350 |
| 3,070,688 | 12/1962 | Glenn, Jr. ............................ | 362/458 |
| 3,174,153 | 3/1965 | Anderson ............................ | 354/126 |
| 3,200,730 | 8/1965 | Neier .................................... | 362/16 |
| 3,417,685 | 12/1968 | Koto et al. .......................... | 354/126 |
| 3,674,648 | 7/1972 | Soli ...................................... | 362/458 |
| 4,034,387 | 7/1977 | Ohtaki et al. ....................... | 354/126 |
| 4,144,556 | 3/1979 | Bond .................................... | 362/347 |
| 4,241,382 | 12/1980 | Daniel ................................. | 362/350 |
| 4,274,131 | 6/1981 | Praausma ............................ | 362/356 |
| 4,526,546 | 7/1985 | Schaeffer ............................ | 362/809 |

Primary Examiner—Raymond A. Nelli
Attorney, Agent, or Firm—Fleit, Jacobson, Cohn & Price

[57] ABSTRACT

When examing visually uneven surfaces the problem is the disappearing of the areas remaining in the shade from the picture. To the lighting device in accordance wiht the invention for illumination of and elimination of shades from uneven surface (1) belong a source of light (2), a mainly globular reflecting contrivance (3), the interior surface of which is equipped with reflecting material, and to which openings (4, 5) for the examining of the surface and holes (6) for conducting of the light into the reflecting contrivance are formed, as well as a reflector element (7) for reflecting of light through the opening (4) into the reflecting contrivance.

4 Claims, 2 Drawing Figures

LIGHTING DEVICE

The object of the invention is a lighting device for illumination of an uneven surface and for elimination of shades.

The disadvantage at the examination of uneven surfaces is, that the areas remaining within the shades of the parts protruding from the surface are not clearly visible. Particularly in works requiring great measuring accuracy this problem is present. Especially at the examining of uneven metal surfaces the shades cause great inconvenience to the accuracy of the examination. One phase e.g. in the control of the cards is the visual observation of the surface. Hereby the surface of the conductor wire appears very uneven. When the surfaces of the conductor wires are smooth and the conductor wires being narrow, not suficient light is obtained on the insulator surface next to the conductor wire. In particular when using conductor wires with tin-lead coatings insufficiently clear results are achieved.

Nowadays different lighting devices have been developed for illumination of surfaces, but these devices are complicated, and the resolution capability achievable with them is not always sufficient.

The aim of the invention is to bring forth a lighting device, which eliminates disadvantages connected with the control of uneven surfaces. In particular the aim of the invention is to bring forth a lighting device, with the help of which the uneven surfaces are illuminated to a sufficient degree for visual examination. Additionally the aim of the invention is to bring forth a lighting device, which is suitable for the automatic visual control of the cards and which is simple as well as easy to produce and to use.

The aim of the invention is accomplished by means of the lighting device, which is mainly characterized in that, what is presented in the part of claims.

According to the invention to the lighting device belongs a source of light, a mainly globular reflecting contrivance, to be positioned at a distance from the source of light and the surface to be examined, and which is equipped with openings for examining and illumination of the surface and with holes for leading of the light into the reflecting contrivance, and the interior surface of which is covered with reflecting substance, as well as a reflector element positioned close to the opening in order to reflect the light through the opening inside the reflecting contrivance. Hereby the light coming into the reflecting contrivance is reflected from the walls of the globe and because the contrivance is placed close to the surface to be examined the reflected beams of light come from different directions onto the surface and illuminate the unevennesses on the surface.

According to the invention the reflector element is favourably a semi-permeable mirror, which is placed at the opening positioned on the side of the reflecting contrivance opposite to the surface, between the reflecting contrivance and the control device. Through illuminating of the mirror from the side and the interior surface of the reflecting contrivance through the holes made in its sides an even illumination on the surface is achieved and the shades caused by the uneven surfaces are reduced. A lighting device in accordance with the invention improves at the examining of the surface the resolution capability particularly at the automatic picture processing, in which it is aimed to identify the conduction and the insulation areas of the cards by means of signals from the camera. The presented solution is applicable also for illumination of other uneven surfaces as well in a dependable way.

Figure 2:
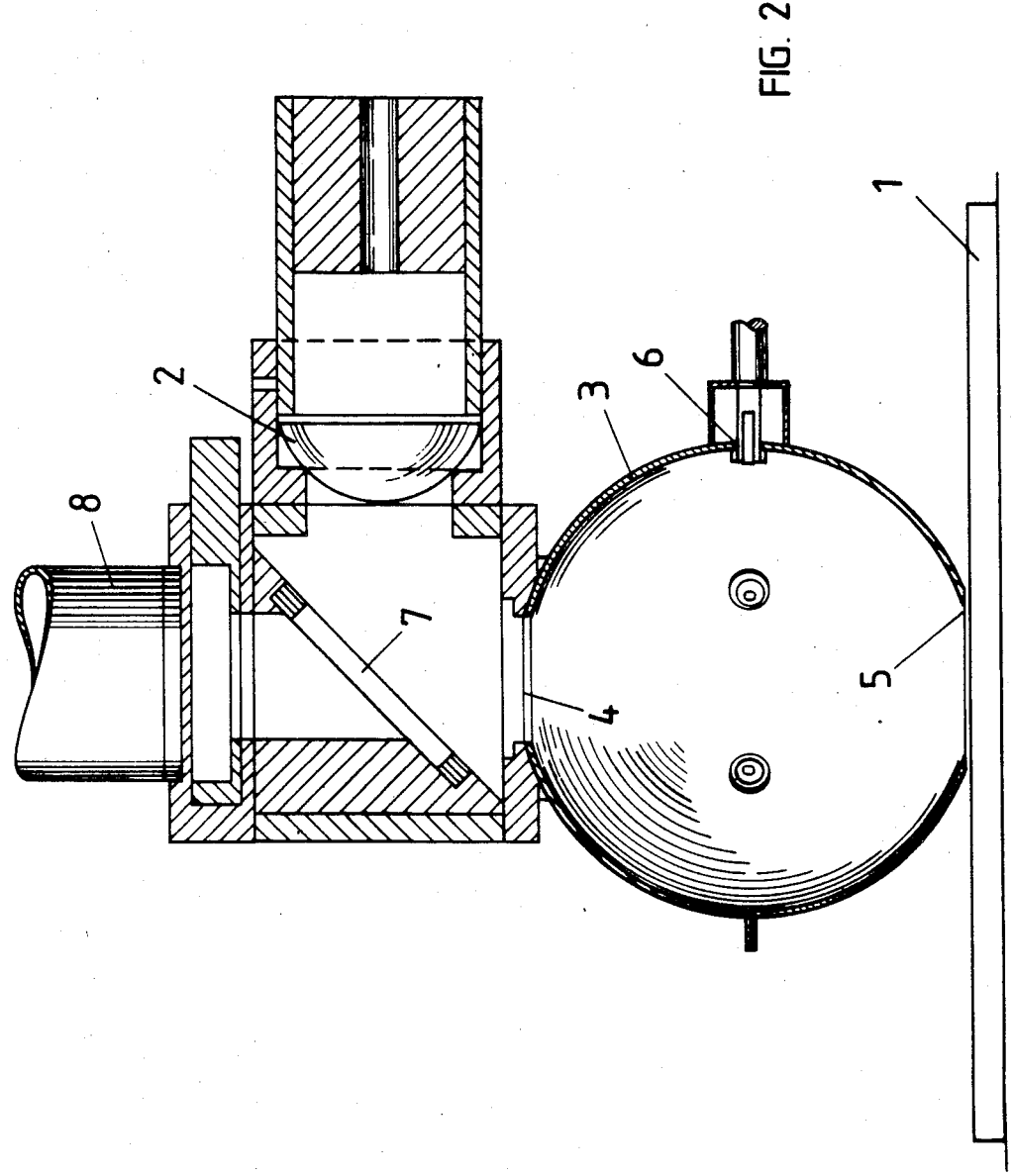

In the following the invention is explained by referring to the attached drawing, in which FIG. 1 presents one application of the device in accordance with the invention in a perspective picture, and FIG. 2 presents one application of the device in accordance with the invention seen from the side and in section. In the applications presented in FIGS. 1 and 2 the lighting device is used for illumination of the card surface 1. The reflecting contrivance 3 is a globular element, which is placed at a short distance from the surface of the card 1. The interior surface of the reflecting contrivance is covered with a diffusedly reflecting material and the reflecting contrivance is equipped with the openings 4, 5 for photographing and the leading of the light as well as the holes 6 for leading of the light into the reflecting contrivance. As the source of light 2 in these applications is used luminous fibre, which is drawn to the immediate neighbourhood of hole and openings 4, 6 in the reflecting contrivance. As a source of light 2 also other known light 2 sources can be used, which are positioned at a distance from the reflecting contrivance. Additionally to the device belongs a semi-permeable mirror 7, which is placed at the opening 4 between the reflecting contrivance and the as a control device acting camera 8. The openings 4, 5 are located on the opposite sides of the reflecting contrivance and when the device is in the measuring position the opening 5 is close to the surface to be measured. The holes are in this application made on the sides of the reflecting contrivance at a distance from each other.

When using the lighting device the light is pointed from the source of light 2 at the reflecting contrivance, where the semi-permeable mirror reflects the light coming on it inside the reflecting contrivance through the opening 4 and a part of the light comes into the reflecting contrivance through the holes 6. The light is reflected from the reflecting interior surface of the contrivance and through the opening 5 on the surface of the card comes light from several different directions. The light reflected from the surface of the card goes through the reflecting contrivance and through the mirror and with the help of the camera the picture is recorded and by means of the picture the conducting and the insulating areas of the card are examined visually.

The invention is not limited to the presented application only, but it can vary within the limits of the patent claims.

What is claimed is:

1. Lighting device for illumination of an uneven surface (1) and elimination of shaded areas on said surface comprising a source of light (2), a substantially spherical reflecting contrivance (3) to be located at a given distance from said source of light, the interior surface of said spherical reflecting contrivance being provided with a reflecting material, said spherical reflecting contrivance being provided with a reflecting coating and openings (4), (5) formed opposite one another to permit both visual examination and illumination of said uneven surface (1) and being further provided with holes (6) to conduct light to the interior of said spherical reflecting contrivance, said device including a reflector element (7) located close to said opening (4) for reflecting of light through said opening into said spherical reflecting contrivance.

2. Lighting device according to claim 1, characterized in, that the device is associated with a surface control unit (8) and, that the openings of the reflecting contrivance are positioned in such a manner that said opening 5 is located close to the surface to be examined when using the device and the other said opening (4) is open in the direction of the control unit (8).

3. Lighting device according to claim 1 characterized in, that the reflector element (7) includes a semi-permeable mirror.

4. Lighting device according to claim 1, characterized in, that said holes (6) spaced apart are located on the sides of the reflecting contrivance at a distance from each other.

* * * * *